US009915143B2

(12) United States Patent
Hallundbæk et al.

(10) Patent No.: US 9,915,143 B2
(45) Date of Patent: Mar. 13, 2018

(54) DOWNHOLE TOOL FOR DETERMINING FLOW VELOCITY USING MEASUREMENTS FROM A TRANSDUCER AND A PLURALITY OF ELECTRODES

(71) Applicant: WELLTEC A/S, Allerød (DK)

(72) Inventors: Jørgen Hallundbæk, Græstead (DK); Jimmy Kjærsgaard-Rasmussen, Birkerød (DK)

(73) Assignee: WELLTEC A/S, Allerød (DK)

( * ) Notice: Subject to any disclaimer, the term of this patent is extended or adjusted under 35 U.S.C. 154(b) by 194 days.

(21) Appl. No.: 14/350,455

(22) PCT Filed: Oct. 30, 2012

(86) PCT No.: PCT/EP2012/071473
§ 371 (c)(1),
(2) Date: Apr. 8, 2014

(87) PCT Pub. No.: WO2013/064494
PCT Pub. Date: May 10, 2013

(65) Prior Publication Data
US 2014/0260589 A1    Sep. 18, 2014

(30) Foreign Application Priority Data

Oct. 31, 2011    (EP) .................................... 11187276

(51) Int. Cl.
*E21B 47/10*    (2012.01)
*G01F 25/00*    (2006.01)
(Continued)

(52) U.S. Cl.
CPC .......... *E21B 47/101* (2013.01); *E21B 47/102* (2013.01); *G01F 1/662* (2013.01);
(Continued)

(58) Field of Classification Search
CPC .. E21B 47/101; E21B 47/102; G01F 25/0007; G01F 1/662; G01F 1/663;
(Continued)

(56) References Cited

U.S. PATENT DOCUMENTS 3,603,145 A * 9/1971 Morris .................. E21B 47/101
73/152.32
3,614,725 A * 10/1971 Moran .................... G10K 11/34
181/104

(Continued)

FOREIGN PATENT DOCUMENTS

CN    1882853 A    12/2006
EP    1 936 112    6/2008
(Continued)

OTHER PUBLICATIONS

Carlson et al, Vortex Imaging Using Two-Dimensional Ultrasonic Speckle Correlation, 2001, IEEE.*
(Continued)

*Primary Examiner* — Peter Macchiarolo
*Assistant Examiner* — David L Singer
(74) *Attorney, Agent, or Firm* — Nixon & Vanderhye PC

(57) ABSTRACT

A downhole tool may include a tool housing extending along a longitudinal axis and having a circumference which is perpendicular to the longitudinal axis, the tool housing being adapted to be lowered into the inside of the borehole or borehole casing. The downhole tool may include a longitudinal transducer for transmitting a probing signal longitudinally from an end part of the tool housing into a fluid flowing in said borehole or borehole casing and for receiving a reflected signal reflected from reflective entrained surfaces in the fluid flowing along a longitudinal direction towards the end part of the tool housing. The downhole tool may include a plurality of electrodes arranged spaced apart
(Continued)

around the longitudinal axis in the periphery of the downhole tool so that the fluid flows between the electrodes and a borehole wall or borehole casing wall.

24 Claims, 8 Drawing Sheets

(51) Int. Cl.
  *G01F 1/66* (2006.01)
  *G01N 27/22* (2006.01)
(52) U.S. Cl.
  CPC .............. *G01F 1/663* (2013.01); *G01F 1/667* (2013.01); *G01F 1/668* (2013.01); *G01F 25/0007* (2013.01); *G01N 27/221* (2013.01)
(58) Field of Classification Search
  CPC ............ G01F 1/667; G01F 1/668; G01F 1/66; G01N 27/221; G01N 27/22
  USPC ....................................................... 73/152.32
  See application file for complete search history.

(56) References Cited

U.S. PATENT DOCUMENTS

| | | | | |
|---|---|---|---|---|
| 4,435,978 A * | 3/1984 | Glatz | ................. | E21B 47/1005 166/250.01 |
| 4,905,203 A | 2/1990 | Sims et al. | | |
| 4,947,683 A | 8/1990 | Minear et al. | | |
| 4,975,645 A * | 12/1990 | Lucas | ................... | E21B 47/102 324/324 |
| 5,777,278 A * | 7/1998 | Bednarczyk | .......... | E21B 47/101 166/264 |
| 8,044,821 B2 * | 10/2011 | Mehta | ..................... | E21B 47/12 340/855.5 |
| 2005/0150655 A1 * | 7/2005 | Duong | ................... | E21B 47/01 166/249 |
| 2006/0054354 A1 * | 3/2006 | Orban | ....................... | E21B 4/18 175/40 |
| 2012/0273270 A1 * | 11/2012 | Rasheed | ............... | E21B 44/005 175/24 |

FOREIGN PATENT DOCUMENTS

| | | |
|---|---|---|
| RU | 1 802 100 A1 | 3/1993 |
| WO | WO 97/46792 | 12/1997 |

OTHER PUBLICATIONS

Xie et al, Electrical capacitance tomography for flow imaging: system model for development of image recontstruction algorithms and design of primary sensors, IEE Proceedings-G, vol. 139, No. 1, Feb. 1992.*

Huang et al, Design of sensor electronics for electrical capacitance tomography, IEE Proceedings—G, vol. 139, No. 1, Feb. 1992.*

Notification Concerning Transmittal of International Preliminary Report on Patentability, International Preliminary Report on Patentability, Written Opinion, dated May 6, 2014, 12 pages.

Carlson et al., "Vortex imaging using two-dimensional ultrasonic speckle correlation", *2001 IEEE Ultrasonics Symposium Proceedings*, vol. 1, 7 Oct. 2001, pp. 559-562.

International Search Report for PCT/EP2012/071473, dated Feb. 19, 2013.

Written Opinion of the ISA for PCT/EP2012/071473, dated Feb. 19, 2013.

* cited by examiner

US 9,915,143 B2

DOWNHOLE TOOL FOR DETERMINING FLOW VELOCITY USING MEASUREMENTS FROM A TRANSDUCER AND A PLURALITY OF ELECTRODES

This application is the U.S. national phase of International Application No. PCT/EP2012/071473 filed 30 Oct. 2012 which designated the U.S. and claims priority to EP Patent Application No. 11187276.8 filed 31 Oct. 2012, the entire contents of each of which are hereby incorporated by reference.

FIELD OF THE INVENTION

The present invention relates to a downhole tool for determining a flow velocity of a fluid in an inside of a borehole or borehole casing. The present invention also relates to a downhole system comprising the downhole tool according to the invention for determining the flow velocity of fluid as well as to a method of determining a flow velocity of a fluid surrounding a tool in a borehole.

BACKGROUND ART

In production logging, flow measurements are very important to gain information on how much and where a well is producing. Typically, a well comprises a plurality of branches, and flow meters are lowered into the well in order to get a view of how much and from which of these branches the well is producing or not producing. Furthermore, unwanted fluids, such as water, may enter the well through fractured casings or enter the well together with other borehole fluids and subsequently end up as unwanted depositions in some sections of the well. This may lead to problems such as water locking in gas wells. Therefore, flow measurements are used to enable the user to map and characterise important flow patterns in a well. In recent years, the old impeller type flow meters have gradually been replaced by Doppler-based flow meters. In general terms, the Doppler-based flow meters take advantage of the change in frequency of a sound wave when a sound wave is transmitted from the flow meter into a fluid and then reflected off by a moving particle, since the change is proportional to the velocity of the particle and thereby proportional to the velocity of the fluid. These types of flow meters have great advantages over the old impeller type flow meters. Doppler-based flow meters have an increased mechanical durability, and they are more versatile for various flow regimes etc. However, Doppler flow meters only provide a reasonable estimate of the flow during relatively well-defined flow patterns and hence provide uncertainty to the user when the user requires accurate and consistent knowledge of the actual flow of fluids downhole to be able to make efficient and relevant decisions based on this knowledge.

SUMMARY OF THE INVENTION

It is an object of the present invention to wholly or partly overcome the above disadvantages and drawbacks of the prior art. More specifically, it is an object to provide an improved downhole tool capable of determining flow velocities of fluids in more complex flow patterns and in mixed fluids in an inside of a borehole or borehole casing.

The above objects, together with numerous other objects, advantages, and features, which will become evident from the below description, are accomplished by a solution in accordance with the present invention by a downhole tool for determining a flow velocity of a fluid in an inside of a borehole or borehole casing, comprising:

- a tool housing extending along a longitudinal axis and having a circumference which is perpendicular to the longitudinal axis, said tool housing being adapted to be lowered into the inside of the borehole or borehole casing,
- a longitudinal transducer transmitting a probing signal substantially longitudinally from an end part of the tool housing into a fluid flowing in said borehole or borehole casing so that the transmitted probing signal is exposed to reflective entrained surfaces in the flowing fluid, and the longitudinal transducer receiving a reflected signal reflected substantially from reflective entrained surfaces in the fluid flowing in said well along a longitudinal direction towards the end part of the tool housing, whereby the flow velocity of the fluid may be extracted from consecutively received reflected signals (RS),
- a plurality of electrodes arranged spaced apart around the longitudinal axis in the periphery of the tool so that the fluid flows between the electrodes and a borehole wall or borehole casing wall, and
- a measuring means for measuring the capacitance between two electrodes in all combinations giving $n*(n-1)/2$ capacitance measurements for n electrodes, wherein the downhole tool has a space between every two electrodes, which space is substantially filled up with a non-conductive means in order to determine properties of the fluid from which the flow velocity is extracted.

In an embodiment, the fluid velocity may be used for adjusting the determination of the properties of the fluid, or the properties of the fluid may be used for adjusting the fluid velocity.

In another embodiment, the velocity of the fluid may be extracted from consecutively received reflected signals by application of the Doppler principle.

Furthermore, the velocity of the fluid may be extracted from consecutively received reflected signals (RS) by application of Ultrasonic speckle velocimetry.

In yet another embodiment, the probing signal transmitted by the transducer may be an acoustic signal.

Moreover, the downhole tool may comprise a plurality of transducers arranged at the end part of the tool housing spaced apart around the longitudinal axis, each transducer transmitting and receiving in a predefined direction.

Furthermore, the transducer part of the tool may be rotated around the longitudinal axis.

Also, the frequency of the transmitted probing signal may be a sonic signal in the range between 40 KHz and 5 MHz, more preferably between 0.5 MHz and 3 MHz, or even more preferably between 1.5 MHz and 2.5 MHz.

Moreover, a transmitting and receiving angle of the transducer(s) may be in the range of 0-10 degrees, more preferably 1-7 degrees, or even more preferably 2-5 degrees from the longitudinal axis.

The downhole tool according to the present invention may further comprise a dimension means, such as a centraliser tool or a caliper, such as a multifinger caliper, for determining the diameter of the borehole or borehole casing.

Further, the downhole tool may comprise a computation and data storing unit for processing flow and capacitance measurements measured by the transducer(s) and electrodes.

The downhole tool as described above may further comprise at least a first radial transducer transmitting a radial probing signal away from a central part of the tool housing towards the casing wall and at least a second radial transducer arranged on the central part spaced away from the first radial transducer, said second radial transducer receiving a reflected signal being the radial probing signal reflected by the casing wall.

Said second radial transducer may be arranged on the central part spaced away from the first radial transducer along the longitudinal axis of the tool.

Also, the downhole tool according to the present invention may comprise an anemometer, such as a constant temperature anemometer or an impeller flow meter.

The present invention further relates to a downhole system comprising:
a wireline,
a tool string,
a driving unit, and
further comprising a downhole tool for determining the flow velocity of a fluid in a borehole.

The downhole system according to the present invention may further comprise an operational tool such as a logging tool, a key tool, a milling tool or a drilling tool.

The present invention further relates to a method of determining a flow velocity of a fluid surrounding a tool in a borehole, comprising the steps of:
transmitting a probing signal substantially along a longitudinal axis of the tool from an end part of the tool housing by a longitudinal transducer,
receiving a reflected signal substantially in a longitudinal direction by the longitudinal transducer,
measuring a capacitance in a capacitance measurement between at least two electrodes, thereby determining properties of the fluid surrounding the tool effecting the capacitance between said at least two electrodes, such as the dielectric constant of the fluid,
determining a calculated flow velocity of the flowing fluid from the transmitted probing signals and received signals and information on the fluid obtained from the capacitance measurement,
sending a set of flow and capacitance measurements data to a computation and data storing unit, and
calculating the flow velocity of the fluid.

Also, the method of determining a flow velocity of a fluid surrounding a tool in a borehole may comprise the step of measuring a set of calibration flow and capacitance measurements in a substantially vertical part of the borehole above a heel of the borehole.

Moreover, said method may further comprise the step of sending at least part of the set of measurements of flow and capacitance measurements to an uphole data receiving means for being received by a user.

Additionally, the method may comprise the steps of:
determining the properties of the fluid surrounding the tool by measuring the capacitance between at least two electrodes, and
selective choice of time intervals in which Doppler shifts are measured so that a scattering velocity profile is determined based on said capacitance measurements.

Finally, the method according to the present invention may further comprise the step of sending data obtained by the capacitance measurements to the user uphole only if the calculated flow velocity falls outside a predefined range.

BRIEF DESCRIPTION OF THE DRAWINGS

The invention and its many advantages will be described in more detail below with reference to the accompanying schematic drawings, which for the purpose of illustration show some non-limiting embodiments and in which.

All the figures are highly schematic and not necessarily to scale, and they show only those parts which are necessary in order to elucidate the invention, other parts being omitted or merely suggested.

DETAILED DESCRIPTION OF THE INVENTION

Figure 1:
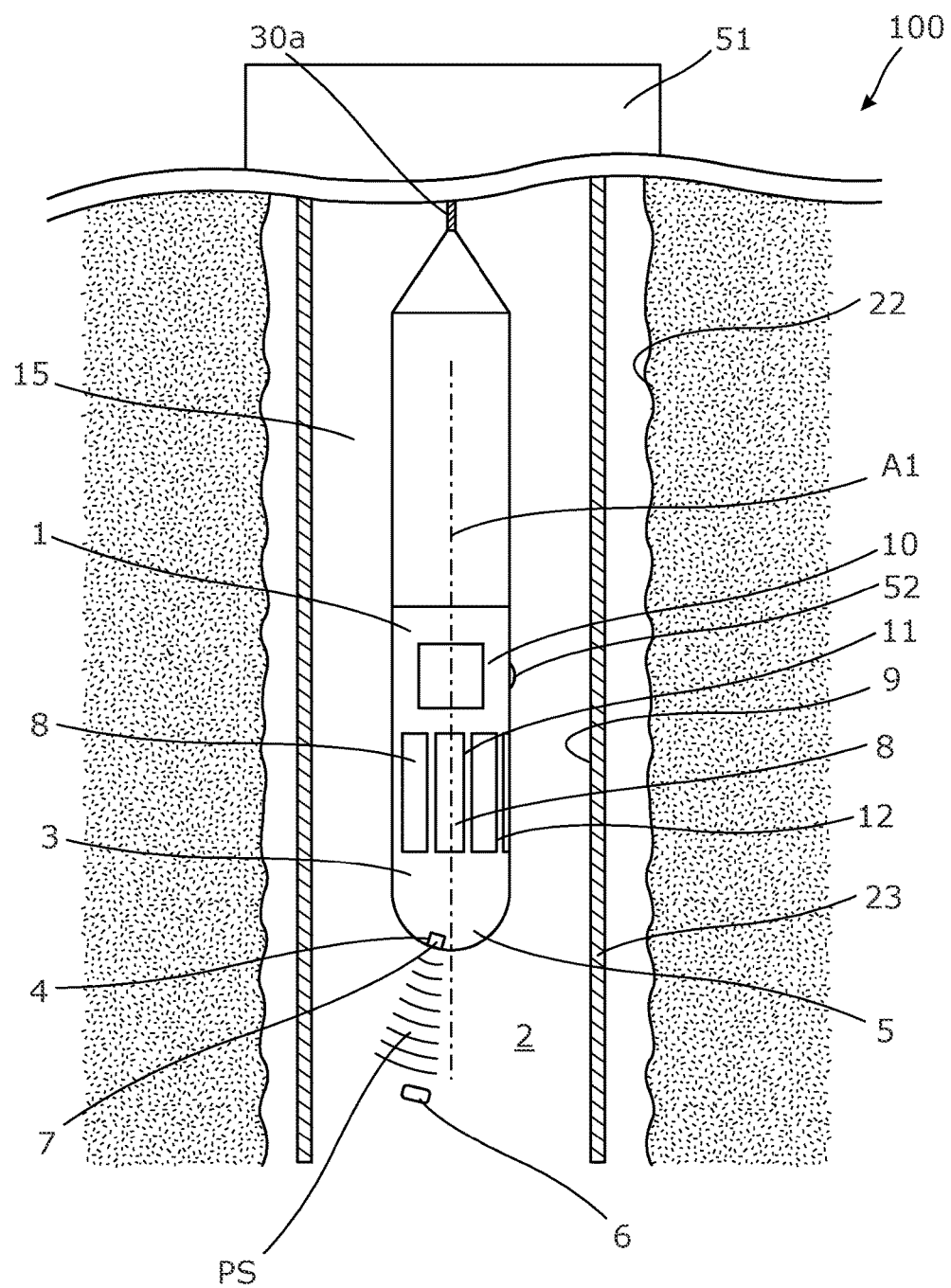
FIG. 1 shows a downhole tool string with a tool for determining flow velocities of fluids and furthermore illustrates a probing signal transmitted from the tool.
Figure 2:
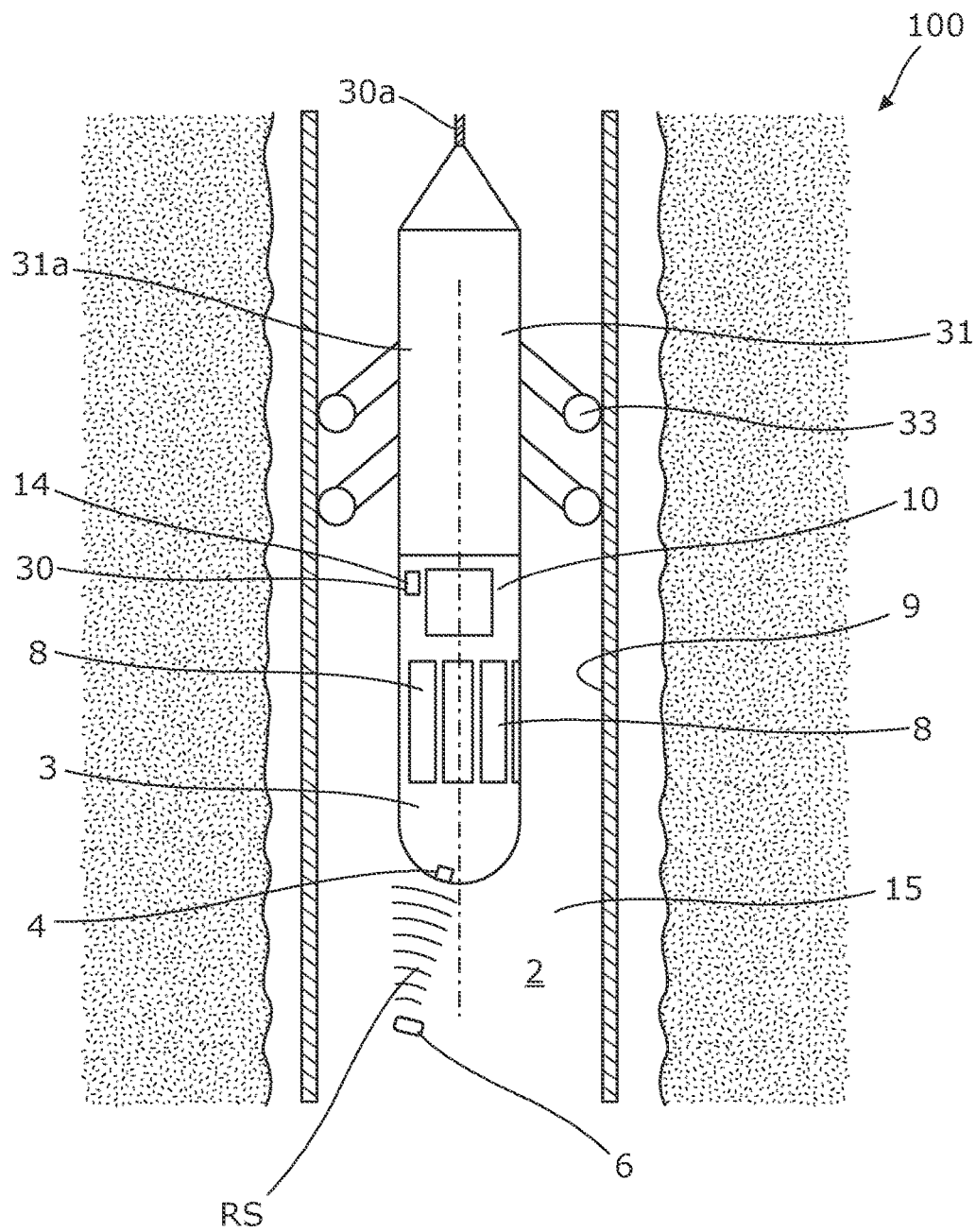
FIG. 2 shows a downhole tool string with a tool for determining flow velocities of fluids and furthermore illustrates a reflected signal from an entrained surface in a fluid surrounding the tool string.

FIG. 1 shows a downhole tool 1 for determining a flow velocity $V_f$ of fluids 15 inside 2 of a borehole 22 or borehole casing 23. A tool housing 3 extends along a longitudinal axis A1 with a circumference in a cross-sectional plane which is perpendicular to the longitudinal axis so that the tool may be lowered into the borehole 22 or borehole casing 23. A longitudinal transducer 4 is arranged at an end part 5 of the tool 1. The longitudinal transducer is capable of transmitting a probing signal PS substantially in the longitudinal axis from the end part 5 of the tool housing 3 into a fluid 15 flowing in the borehole 22 or borehole casing 23. When the fluid 15 comprises reflective entrained surfaces 6, such as gas bubbles or particles, the probing signal PS exposed to these reflective entrained surfaces 6 in the flowing fluid 15 will be reflected towards the tool. The longitudinal transducer 4 will therefore receive a reflected signal RS reflected substantially from a longitudinal direction towards the longitudinal transducer 4 arranged on the end part 5 of the tool housing 3, as shown in FIG. 2. The reflected signal RS received by the longitudinal transducer contains information from which the velocity of the entrained surface reflecting the probing signal can be calculated by comparing the probing signal and the reflected signal. The deduction of such information, e.g. by application of the Doppler principle, is well-known in the art, e.g. from U.S. Pat. No. 4,947,683 or other types of velocimetry, e.g. based on ultrasonic speckle velocimetry, also known as echo particle tracking velocimetry. Ultrasonic speckle velocimetry is based on the same principles as other Particle Tracking Velocimetry (PTV) techniques, e.g. the optical method of flow visualisation (Particle Image Velocimetry (PIV)). Ultrasonic speckle velocimetry is based on the same principles as PIV but uses the echo of ultrasonic signals instead of reflected light. PIV may be used to obtain instantaneous velocity measurements and related properties in fluids. The fluid comprises tracer particles which, for sufficiently small particles, are assumed to faithfully follow the flow dynamics. The fluid with entrained particles is illuminated so that particles are visible and when using ultrasonic speckle velocimetry exposed to ultrasonic signals. The motion of the tracer particles is used to calculate speed and direction (the velocity field) of the flow being studied. With ultrasonic speckle velocimetry, the particles already present in the fluid may be used instead of introducing tracer particles, as the particles only need to be able to reflect the ultrasonic signals.

The main difference between PIV and other techniques like the Doppler shift technique is that PIV produces two-dimensional or even three-dimensional vector fields while the other techniques measure the velocity at one point. During PIV, the particle concentration is such that it is possible to identify individual particles in an image, but not with certainty track it between images. When the particle concentration is so low that it is possible to follow an individual particle, it is called particle tracking velocimetry, while laser speckle velocimetry is used for cases where the particle concentration is so high that it is difficult to observe individual particles in an image.

The downhole tool furthermore comprises a plurality of electrodes 8 arranged spaced apart around the longitudinal axis A1 in the periphery of the tool. Fluid 15 situated between the tool and a borehole 22 or borehole casing wall 9 provides a medium situated between the electrodes 8 such that the capacitance between two electrodes 8 may be measured by a measuring means 10 connected to the electrodes 8. The downhole tool has a space 11 between every two electrodes, said space being substantially filled up with a non-conductive means 12, allowing the measuring means 10 to measure the capacitance between two electrodes 8 in $n*(n-1)/2$ combinations for n electrodes 8.

The capacitance between two electrodes 8 depends on the relative placement of the electrodes and the permittivity of the fluid 15 situated between them. In general, the capacitance depends on the geometry and the permittivity distribution in the annulus between the sensor and the casing. Since the geometry is fixed, any changes measured in the capacitance must be caused by the permittivity distribution between two electrodes. An "image" of all fluids surrounding the tool may thus be created from the capacitance measurements providing information on the different phases or different fluids surrounding the tool.

Figure 3:
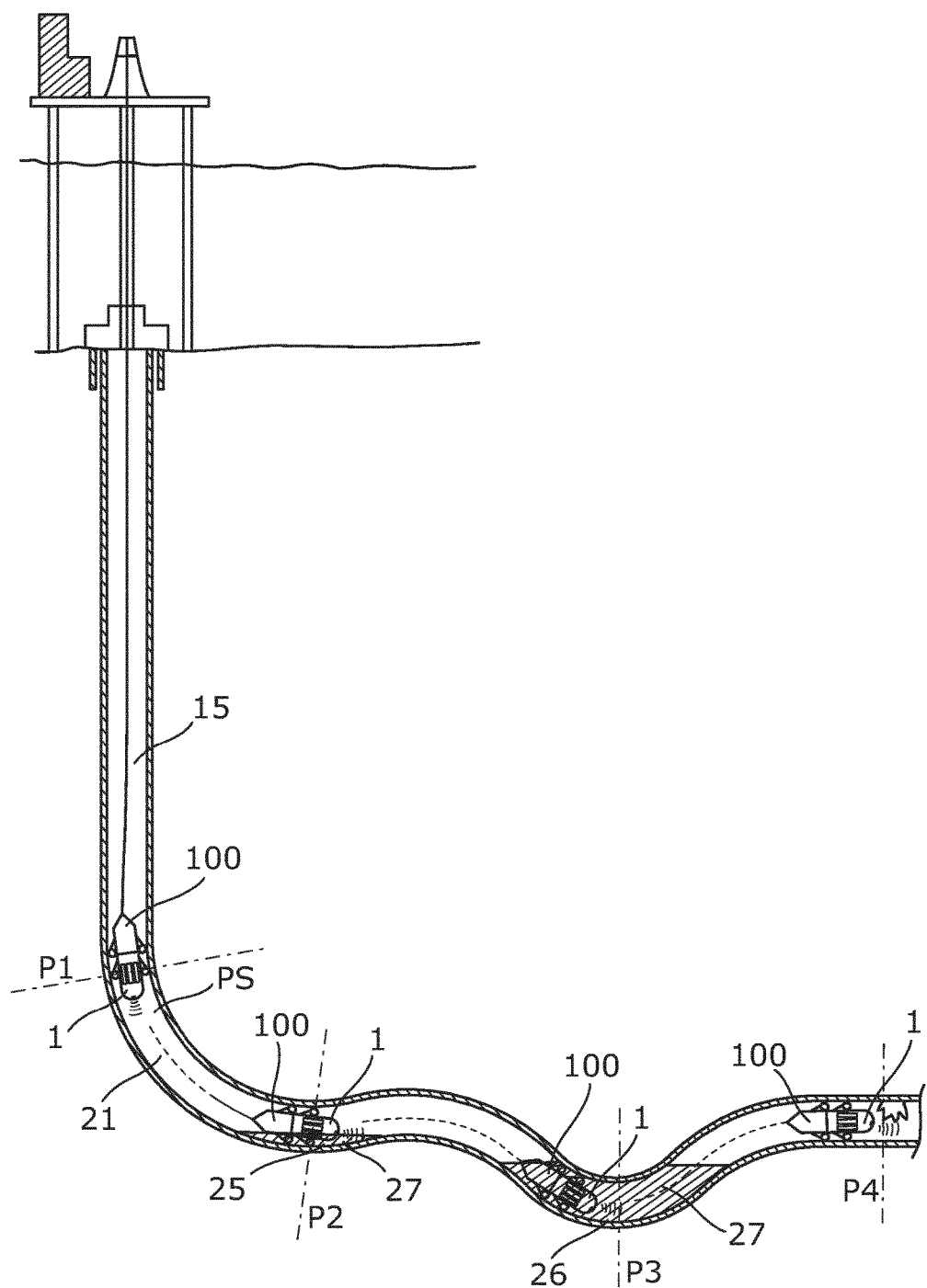
FIG. 3 shows four different positions of a downhole tool string with a tool for determining flow velocities of fluids in a well.

The downhole logging tool 1 is used to obtain information on the flow velocity of fluids 15 in the borehole or borehole casing. This flow velocity may be determined by well-known methods utilising the Doppler principle or ultrasonic speckle velocimetry, however, several other factors influence the fluid flow in a well. Since tools known in the art do not account for these other factors, which will be described in more detail in the following, the measurements are often imprecise or even inconclusive for the user. Other factors influencing the flow velocity or the determination of the flow velocity may be factors such as limited flow in the well due to the well being partially or wholly blocked by other fluids or sediments of solid materials. Limited flow typically arises in horizontal parts of the well, as illustrated in FIG. 3. FIG. 3 shows four different positions of a downhole tool string 100 with a tool 1 for determining flow velocities of fluids 15 in a well. The first position P1 is in a substantially vertical part of the well above the heel 21 of the well. Typically, the flow of fluids 15 in such a part of the well is quite homogeneous and therefore appropriate for a calibration measurement before entering a horizontal part of the well.

Figure 4:
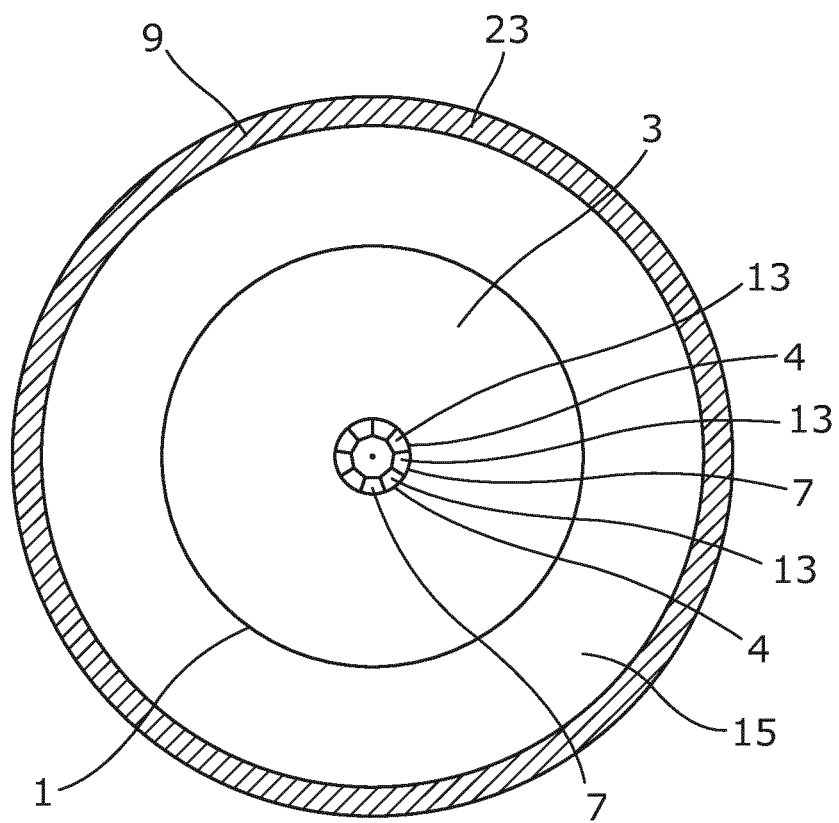
FIG. 4 shows an end view of a downhole tool string with a tool for determining flow velocities of fluids comprising a plurality of transducers.

FIG. 4 shows an end view of a downhole tool string 100 with a tool 1 for determining flow velocities of fluids 15 surrounding the tool string 100. The tool 1 shown in FIG. 4 furthermore comprises a plurality of transducers 7 for transmitting probing signals PS substantially in the longitudinal direction and in radial directions around the longitudinal axis A1 in order to be able to cover angles around the entire circumference of the tool 1 with probing signals. Typically, a plurality of transducers each transmitting signals in only small angle ranges, e.g. below 5 degrees, is placed around the entire circumference of the tool, thereby covering the entire circumference of the tool by representative measurements. As an alternative to the plurality of transducers 7, a transducer may be rotated around the longitudinal axis A1 to cover the entire circumference of the tool 1 with probing signals.

Figure 5:
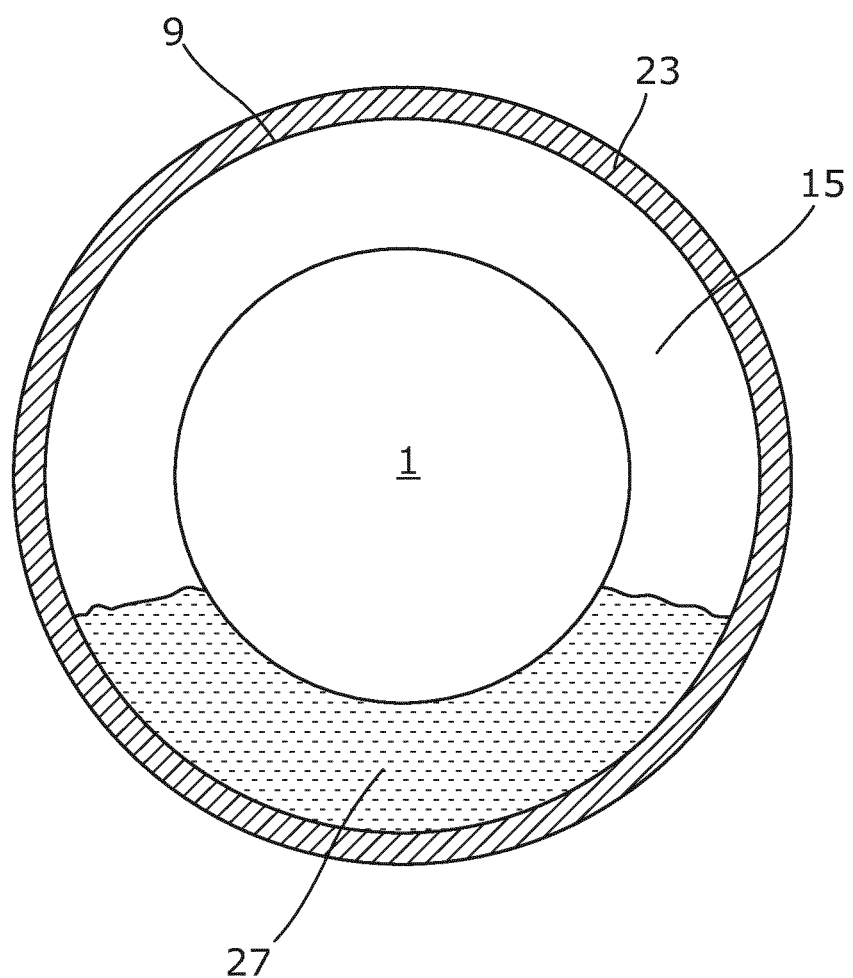
FIG. 5 shows a cross-sectional view of a tool string as shown in FIG. 1 in a borehole casing partially filled with a fluid.

In a second position P2, the tool has been in a substantially horizontal part of the well comprising a first local depth minimum 25 in the well. This first local depth minimum 25 may result in the collection of a limiting volume 27 in the borehole casing 23, such as water in gas or slurries containing heavy particles in a lighter fluid phase or even solid sediments or solid precipitates, all of which limit the diameter of the well at the first local depth minimum, thereby increasing the flow velocity of fluids passing the first local depth minimum. The user placing the tool in the second position P2 will therefore experience from the measurements using the Doppler-shifted probing signal that the flow velocity has increased in this particular region of the well. However, from concurrent capacitance measurements, the user knows that the flow passage in the well is partially limited, and the user may therefore correct appropriately for these deviances. Furthermore, the calculation of the velocity of the flowing fluid may be improved by the capacitance measurements deriving information on the type of fluid flowing, since the Doppler shift of the probing signal depends also on the characteristic impedance of the fluid through which the probing signal propagates. Therefore, the user is provided with a flow velocity corrected for both flow limitations in the well and characteristic impedance of the flowing fluid. FIG. 5 shows a cross-sectional view of a tool string 100 in a borehole casing 23 partially filled with fluid 15 and partially with a limiting volume 27, as described with respect to the second position P2.

When measuring the fluid velocity $V_f$ downhole, sudden changes may be regarded as instabilities of the transducers or transducer measurements by the user situated uphole. However, the instabilities may result from a physical difference of the fluid 15 giving rise to large fluctuations in or even lack of reflected signals RS, e.g. a large volume of gas travelling with a liquid or a local concentration difference of heavy or large particles. Thus, by measuring capacitance simultaneously to measuring the flow velocity, the user knows why sudden changes in signals arise and may act accordingly, e.g. by continuing measuring in the position of the instabilities to check if the instabilities are caused by the moving fluid and therefore disappear after a given time, or if the instabilities are characteristic of the position in the well and therefore continue in time.

Figure 6:
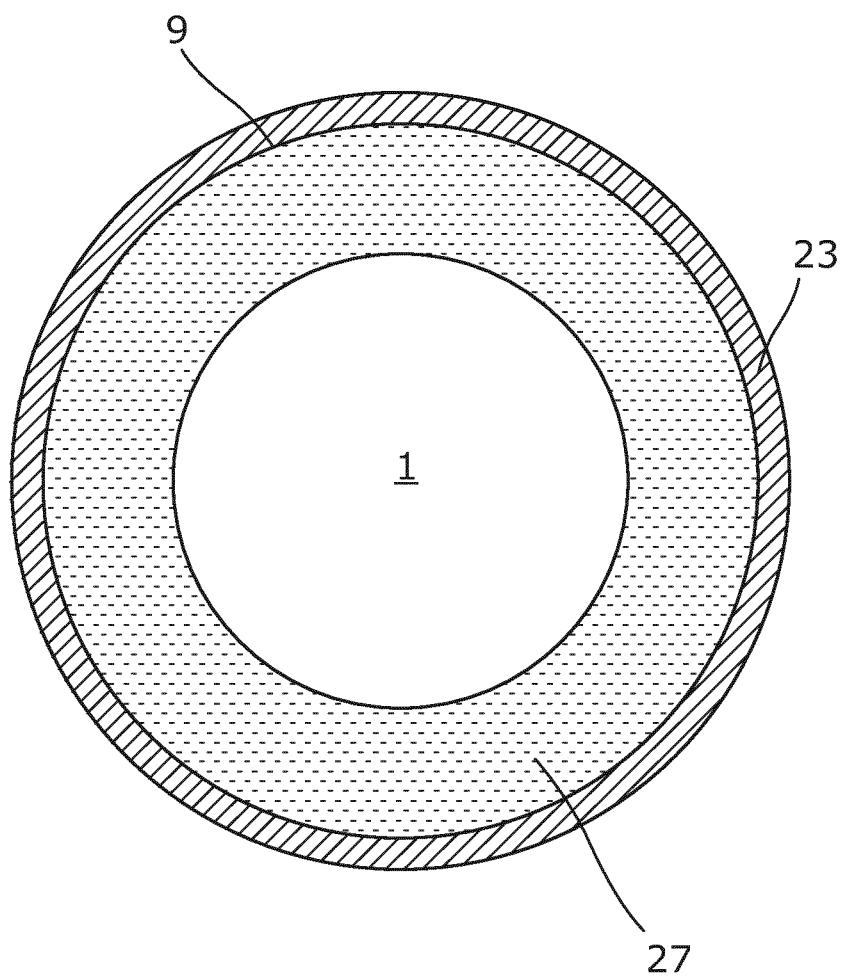
FIG. 6 shows a cross-sectional view of a tool string as shown in FIG. 1 in a borehole casing filled with a fluid.

Moving further into the well, the tool 1 reaches second local depth minimum 26 at a third position P3. This second local depth minimum 26 is deeper than the first local depth minimum 25, and the limiting volume 27 therefore completely blocks the well. An example of such a situation may be the presence of water in gas wells. If a local depth minimum, such as the second local depth minimum 26 in FIG. 3 at the third position P3, is filled up with water, the pressure may build up in the gas furthest into the well until the pressure of the gas is high enough to force its way past the water at the local depth minimum. The water therefore acts as a water lock separating gas present on either side of the water from each other. The effect of such a water lock seen from the perspective of the user uphole when measuring only Doppler shift or an ultrasonic speckle velocimetry signal of the probing signal is a highly irregular signal. First of all, the characteristic impedance of the gas is typically quite different from that of water or any other fluid, and since the calibration measurement made at the first position P1 in this situation was performed in the gas, the measurements of flow velocity performed in water will be off if they are not corrected for the presence of water. Furthermore, the "pressure build-up" furthest into the well and the "pressure release" when the gas is forced past the water result in the water slopping back and forth in this second local depth minimum 26. The calculations of the flow velocity from Doppler-shifted probing signal is made under the assumption that the fluid is flowing in one direction during the measurement, and therefore, when performing the calculation from data measured on a fluid alternating in direction, the result becomes highly irregular. The problem may even be that some measurements seem to be valid whereas consecutive measurements are meaningless. Therefore, combining the Doppler measurements or the ultrasonic speckle velocimetry measurements with the capacitance measurements provides the user with the knowledge that the highly irregular sonic measurements are triggered from measuring in a completely different fluid than expected. Further information to the user regarding local depth minima may be obtained by providing the tool string 100 with a gyroscope 14 and/or accelerometers 30. FIG. 6 shows a cross-sectional view of a tool string 100 in a borehole casing 23 completely filled at the point of cross-section with a limiting volume 27, as described with respect to the third position P3.

In a fourth position P4, a crack 28 in the borehole casing 23 causes an inflow of fluid into the inside 2 of the borehole casing 23, such that the flow of fluids 15 at the fourth position P4 is disturbed. However, again the capacitance measurement will provide information of the presence of another fluid, and hence, the user will know why the sonic measurements may give unexpected or erroneous results.

Figure 7:
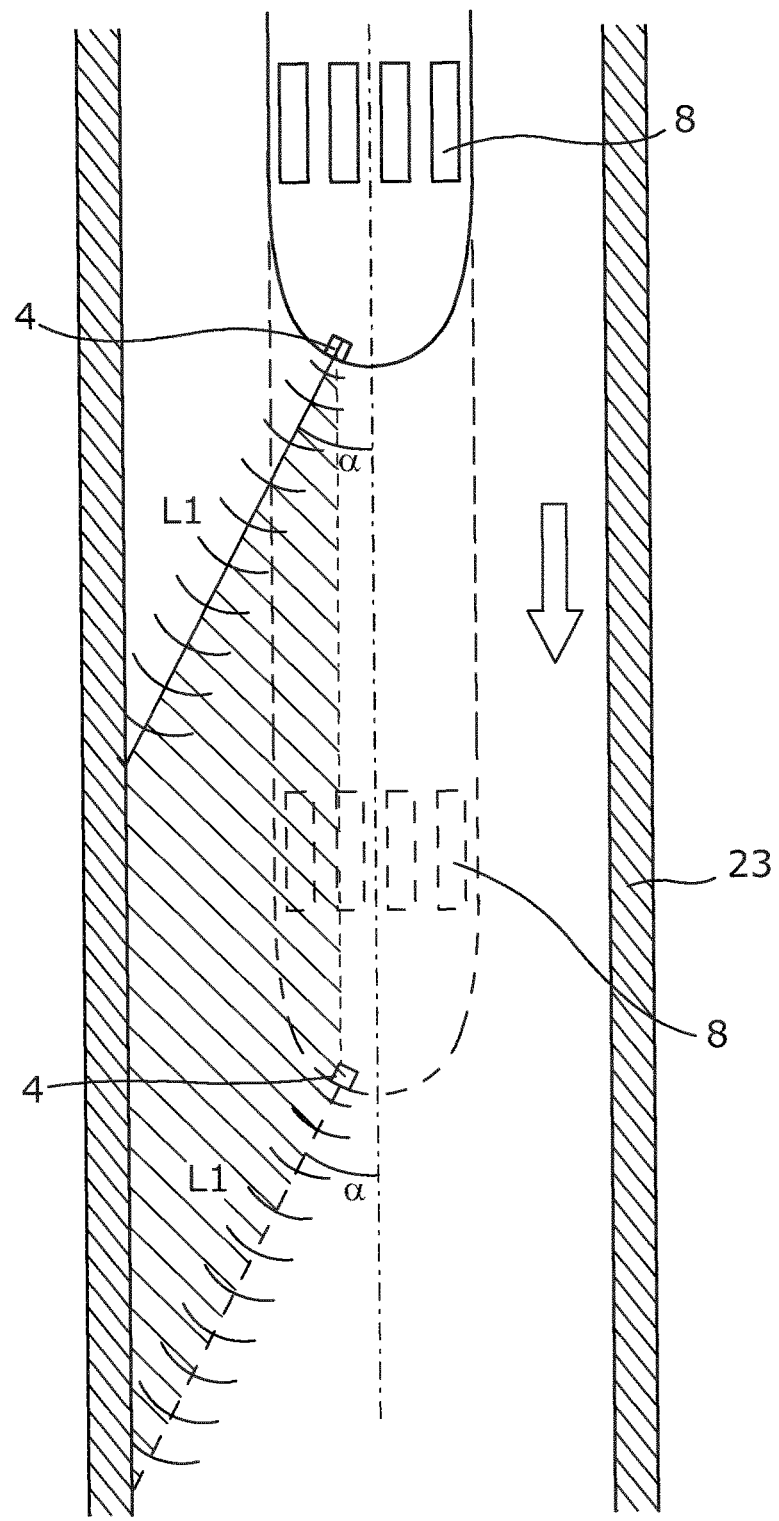
FIG. 7 shows a schematic drawing of the downhole tool transmitting a probing signal at two consecutive times.

FIG. 7 is a schematic drawing of the downhole tool 1 transmitting a probing signal PS at two consecutive times when moving the tool 1 down through the borehole casing 23. As seen in FIG. 7, the probing signal PS is transmitted at an angle α from the longitudinal axis A1. When the tool 1 is moved through the well while measuring at an angle α towards the inner wall 9 of the borehole casing 23, an area of the borehole is swept with the probing signal PS. This enables the user to make a velocity profile of the flow in the borehole and not only measure a single flow velocity as would have been the case if the probing signal PS was sent parallel to the longitudinal axis A1. An advantage of transmitting parallel to the longitudinal axis A1 is to have the full Doppler shift available, however, no information on the velocity profile is gained. To maximise the information gained by a series of consecutive measurements made by the tool 1, the angle α is then adjusted so that a length L1 from the longitudinal transducer 4 to the inner wall 9 of the borehole casing 23 corresponds to a possible distance from which a useful reflected signal RS may be received as a consequence of wavelength of the probing signal PS, impedance of the fluid 15 etc., so that the angle α is minimised to maximise the Doppler shift while still reaching the inner wall 9 of the borehole casing 23 in order to be able to provide a full velocity profile of the fluid 15 inside the borehole casing 23.

In experiments, transmitting frequencies using sonic transducers has proved useful in the ultrasonic range between 40 KHz and 5 MHz, more preferably between 0.5 MHz and 3 MHz, or even more preferably between 1.5 MHz and 2.5 MHz. By increasing the frequency of the probing signal, the resolution is also increased. However, the damping of the signal is also increased, resulting in shorter penetration depth of the probing signal PS into the fluid 15 and vice versa. The mentioned frequencies provide useful results with regard to typical fluids in boreholes, and probing signals PS using the above mentioned frequencies transmitted in angles from the longitudinal axis A1, such as in the range 0-10 degrees, more preferably 1-7 degrees, or even more preferably 2-5 degrees, may provide full velocity profiles of the flow velocity in typical production oil wells. Since small angles may be adequate in small boreholes or if resolution is not crucial, or very large entrained surfaces exist in the fluid and vice versa, the angle and frequency have to be adjusted for each specific application with the above-mentioned effects in mind. The invention is therefore not limited to these intervals, but they provide optimal intervals for the use of tools according to the invention in boreholes having conventional industrial dimensions.

Since information on fluid characteristics is obtained by the capacitance measurements, knowledge on the diameter of the borehole 22 or borehole casing 23 may provide sufficient information to control the frequency and angle of the longitudinal transducer 4 to an optimal combination downhole without prior knowledge of the measuring conditions. Therefore, having a downhole tool further comprising a means 31a for determining the diameter of the borehole or borehole casing, such as a centraliser tool, e.g. a driving unit 31 comprising a driving means 33 having a measure of borehole diameter corresponding to a degree of extraction of the driving means 33, enables the user or an automated measuring procedure to take into account the exact diameter of the borehole 22 or borehole casing 23 at a given point of measuring. Knowing the damping of a given fluid 15 from capacitance measurements using the electrodes 8 and the actual diameter of the borehole 22 or borehole casing 23, the probing signal PS may be modified accordingly to have an optimal frequency and/or an optimal angle α of transmission.

The optimal angle α and operating frequency f depends on the type of fluid and the diameter of the well. If the diameter is known, either from a well schematic or from a local measurement, the fluid type can be determined by the capacitance measurements. The capacitance measurement can thus be utilised to achieve optimal resolution and accuracy of the velocity measurement by altering the frequency and/or angle of the transducers accordingly.

Furthermore, it is also possible to use the velocity information from the transducer, such as an ultrasonic probe, to improve the reconstruction of the permittivity distribution in order to improve the usefulness of the information from the capacitance measurements by knowing at least a velocity probability distribution derived from the ultrasonic measurements.

To be able to optimise data storage and/or control mechanisms of the measurements downhole with only limited access to data transfer through the wireline 30a to the uphole user, a computation and data storing unit 13 for processing flow and capacitance measurements measured by the transducers and electrodes may be comprised in the tool 1. This allows not only automated control mechanisms controlling the measurements, but also enables the user to receive only selected data during downhole operations through the wireline whereas the gross output of data may be stored locally in a storing means also comprised in the tool 1.

Figure 8:
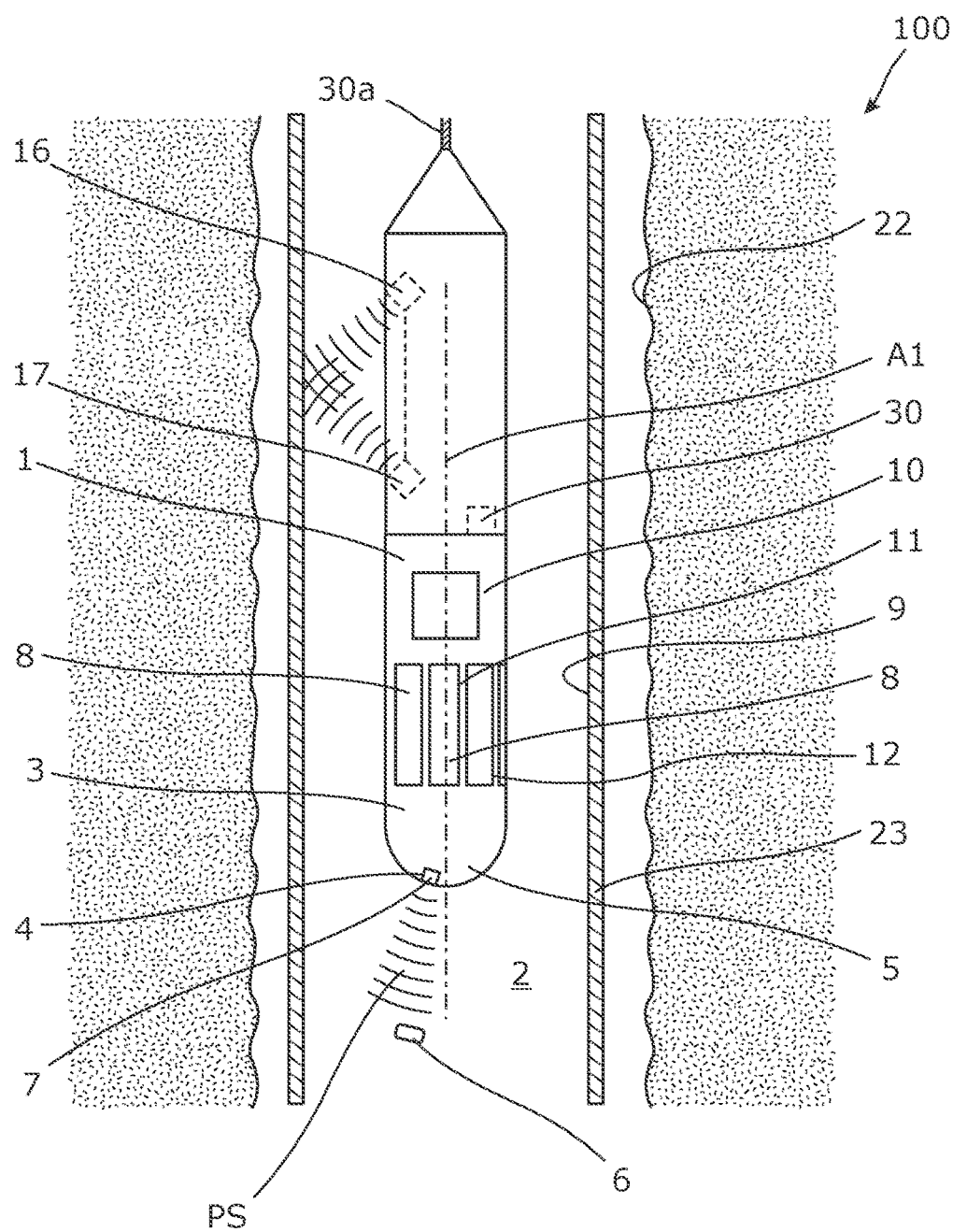
FIG. 8 shows a downhole tool string with a tool for determining flow velocities of fluids and furthermore illustrates several probing signals transmitted from the tool.

As shown in FIG. 8, a way to improve the sonic measurements using the longitudinal transducer 4 is to have the downhole tool furthermore comprising a first radial transducer 16 transmitting a radial probing signal away from a central part of the tool housing towards the casing wall and at least a second radial transducer 17 arranged on the central part spaced away from the first radial transducer 16, said second radial transducer 17 receiving a radial reflected signal from the radial probing signal reflected by the casing wall to perform a time-of-flight measurement. The time-of-flight measurements are based on a calculation of a time period between the transmitted signal and receipt of the reflected signal received after the predetermined time period, and this time period reflects the flow velocity. In FIG. 8, the time-of-flight measurements need a surface like the inner wall 9 of the borehole casing 23 and therefore cannot be made from the end of the tool longitudinally into the fluid 15. Time-of-flight measurements are normally measured along the tool, where the tool 1 limits the flow in the borehole casing 23. The signal-to-noise ratio in the time-of-flight measurement is much higher than the longitudinal measurement using reflections from entrained surfaces. However, measuring radially using time-of-flight measurements may provide the ability to derive variables characteristic of the fluid or fluid flow from both the longitudinal and the radial sets of measurements, and thereby, the user will know these variables with a higher degree of accuracy when using them for calculations of the flow velocity $V_f$ from the longitudinal measurements. Hence, improved accuracy in the calculation of the flow velocity from the longitudinal measurements is obtained. Another way of improving the determination of the flow velocity is by further fitting the downhole tool with an impeller flow meter or a constant temperature anemometer 52 to improve the possibilities of determining the exact characteristics of the fluid surrounding the tool 1. In another embodiment, the transducers may be arranged facing one another, e.g. on arms projecting from the tool, so that the time-of-flight measurements no longer need a surface to bounce on.

The invention also relates to a downhole system comprising both a wireline 30a, a tool string 100, a driving unit 31 and a downhole tool 1 for determining flow velocity ($V_f$) of fluids. As alternatives to wireline operations, the tool 1 may be used in combination with a coiled tubing or self-propelled driving unit, e.g. working on battery power.

Furthermore, the downhole system may comprise an operational tool, such as a logging tool, a key tool, a milling tool, a patching tool or a drilling tool. The downhole tool 1 is appropriate for determining flow velocities downhole. By carrying one or more operational tools on the tool string 100, the user may take appropriate actions as a response to flow measurements indicating e.g. ingress of the water into the borehole casing 23 due to a crack 28, such as setting a patch in the region of the crack by a patching tool.

The invention also relates to a method of determining a flow velocity of a fluid surrounding a tool in a borehole comprising the steps of first transmitting a probing signal substantially longitudinally from an end part of the tool housing by a longitudinal transducer. Due to reflective entrained surfaces 6 comprised within the fluid 15, the probing signal PS is reflected back towards the tool 1 constituting now a reflected signal RS. The longitudinal transducer 4 then receives the reflected signal RS which, compared to the probing signal, has shifted in frequency according to the Doppler principle or receives a recognisable speckle using ultrasonic speckle velocimetry. Furthermore, the capacitance of the fluid 15 is measured in a capacitance measurement between at least two electrodes 8, thereby determining properties of the fluid surrounding the tool affecting the capacitance. The next step of the method is to determine a calculated flow velocity of the flowing fluid by using e.g. the shift in frequency between the transmitted probing signals PS and received signals RS and information on the fluid obtained from the capacitance measurement and finally sending a set of flow and capacitance measurements data to a computation and data storing unit 13, and calculating the flow velocity $V_f$ of the fluid 15 by a means of the computation and data storing unit 13. The method according to the present invention may furthermore comprise a calibrating step which may be performed prior to the operation or during the operation, uphole or downhole, and furthermore in an appropriate position of the well, e.g. in a section of the well having a homogenous flow. When the downhole tool 1 is lowered into the borehole 22 or borehole casing 23, the flow of fluids is typically quite homogeneous in a vertical part of the well above a heel 21 of the well as opposed to a more vertical part of the well below the heel 21. Therefore, in order to have a well-defined calibration of the tool 1, a calibration measurement of the flow velocity according to the above may advantageously be made above the heel 21 of the well. Also, the method according to the invention may comprise a step of sending at least part of the set of flow and capacitance measurements data to an uphole data receiving means 51 in order for the user to follow in situ the determination of flow velocity $V_f$ downhole.

The method according to the invention may further comprise the steps of initially determining the properties of the fluid surrounding the tool by measuring the capacitance between at least two electrodes such that the time intervals in which sonic signals are measured may be selectively chosen based on said capacitance measurements. Due to differences in impedances of different fluids, the time intervals chosen to determine a profile of flow velocities $V_f$ in the fluid 15 may advantageously be selected to match the properties of the fluid being measured.

In downhole operations possibilities of calculation, storing and sending data are always limited due to space limitations and distance from power sources. Therefore, the method according to the present invention may further comprise a step of sending data obtained by the capacitance measurements of the user uphole only if the calculated flow velocity falls outside a predefined range. For the calculation of the flow velocity $V_f$, capacitance data are used to correct the calculations for differences based on fluid properties, but also when the calculations of fluid velocities $V_f$ give very divergent, oscillating or erroneous results, the user needs to know whether or not these results stem from the presence of other fluids, limiting volumes 27 etc. as may become apparent from the capacitance measurements. Since data transfer to the uphole user is limited, the data from the capacitance measurements may be controlled to only transfer to the user when the calculated flow velocity lies outside a predefined range, such that only important data are sent uphole. Alternatively, the capacitance measurements are sent to the user when the capacitance lies outside a predefined range. In order to minimise the data transferred to the uphole user, the amount of data sent to the uphole user may adaptively be compressed such that the amount of data is proportional to the activity in the well, i.e. the more events measured, the more data is transferred to the uphole user.

Transducers may be of type electroacoustic, electromagnetic, electromechanical, electrostatic or radioacoustic, such as loudspeakers, microphones, tactile transducers, piezoelectric crystals, geophones, hydrophones, sonar transponders, antennas, cathodes, micro-electromechanical systems, vibration-powered generators, potentiometers, load cells, accelerometers, strain gauges, string potentiometers etc.

By fluid or well fluid is meant any kind of fluid that may be present in oil or gas wells downhole, such as natural gas, oil, oil mud, crude oil, water, etc. By gas is meant any kind of gas composition present in a well, completion, or open hole, and by oil is meant any kind of oil composition, such as crude oil, an oil-containing fluid, etc. Gas, oil, and water fluids may thus all comprise other elements or substances than gas, oil, and/or water, respectively.

By a casing is meant any kind of pipe, tubing, tubular, liner, string etc. used downhole in relation to oil or natural gas production.

In the event that the tool is not submergible all the way into the casing, a downhole tractor can be used to push the tool all the way into position in the well. The downhole tractor may have projectable arms having wheels, wherein the wheels contact the inner surface of the casing for propelling the tractor and the tool forward in the casing. A downhole tractor is any kind of driving tool capable of pushing or pulling tools in a well downhole, such as a Well Tractor®.

Although the invention has been described in the above in connection with preferred embodiments of the invention, it will be evident for a person skilled in the art that several modifications are conceivable without departing from the invention as defined by the following claims.

The invention claimed is:

1. A downhole tool for determining a flow velocity of a fluid inside of a borehole or borehole casing, comprising:
   a tool housing having a circumferential surface extending along and around a longitudinal axis of the downhole tool, said tool housing being adapted to be lowered into the inside of the borehole or borehole casing;
   a longitudinal transducer configured to transmit a probing signal longitudinally from an end part of the tool housing into a fluid flowing in said borehole or borehole casing so that the transmitted probing signal is exposed to reflective entrained surfaces in the flowing fluid, and to receive a reflected signal reflected from reflective entrained surfaces in the fluid flowing along a longitudinal direction towards the end part of the tool housing;
   a plurality of electrodes arranged spaced apart around the longitudinal axis in the periphery of the circumferential surface of the tool housing so that the fluid flows between the electrodes and a borehole wall or borehole casing wall, wherein the downhole tool has a space between every two electrodes filled up with a non-conductive material; and
   a processing system configured to:
      determine the flow velocity of the fluid from consecutively received reflected signals, and
      determine, using the capacitance between two electrodes in all combinations giving $n*(n-1)/2$ capacitance measurements for n electrodes, properties of the fluid indicating a type of fluid flowing, wherein the determined flow velocity is used for adjusting the determination of the type of fluid flowing or the determined type of fluid flowing is used for adjusting the flow velocity; and
      adjust one or both of a frequency of the transducer and a transmitting angle of the transducer based on the capacitance measurements.

2. A downhole tool according to claim 1, wherein the velocity of the fluid is determined from consecutively received reflected signals by application of the Doppler principle.

3. A downhole tool according to claim 1, wherein the velocity of the fluid is determined from consecutively received reflected signals by application of ultrasonic speckle velocimetry.

4. A downhole tool according to claim 1, wherein the downhole tool comprises a plurality of transducers arranged at the end part of the tool housing spaced apart around the longitudinal axis, each of the plurality of transducers is configured to transmit and receive in a predefined direction respectively.

5. A downhole tool according to claim 1, wherein a frequency of the transmitted probing signal is a sonic signal in the range between 40 KHz and 5 MHz.

6. A downhole tool according to claim 1, wherein a transmitting and receiving angle of the longitudinal transducer is in the range of 0-10 degrees from the longitudinal axis.

7. A downhole tool according to claim 1, wherein the downhole tool further comprises a centraliser tool or a multifinger caliper for determining the diameter of the borehole or borehole casing.

8. A downhole tool according to claim 1, wherein the processing system comprises a computation and data storing unit disposed inside of the tool housing for processing flow and capacitance measurements measured by the longitudinal transducer and the electrodes.

9. A downhole tool according to claim 1, further comprising at least a first radial transducer transmitting a radial probing signal away from a central part of the tool housing towards the casing wall and at least a second radial transducer arranged on the central part spaced away from the first radial transducer, said second radial transducer receiving a reflected signal being the radial probing signal reflected by the casing wall.

10. A downhole tool according to claim 1, further comprising a constant temperature anemometer or an impeller flow meter.

11. A downhole system comprising:
    a wireline;
    a tool string;
    a driving unit; and
    a downhole tool for determining the flow velocity of a fluid in a borehole or borehole casing according to claim 1.

12. A downhole system according to claim 11, furthermore comprising a logging tool, a key tool, a milling tool or a drilling tool.

13. A method of determining a flow velocity of a fluid surrounding a tool in a borehole, the tool comprising a tool housing having a circumferential surface extending along and around a longitudinal axis of the tool, a longitudinal transducer, and a plurality of electrodes arranged spaced apart around the longitudinal axis in the periphery of the tool, the method comprising:
    transmitting, by the longitudinal transducer, a probing signal along a longitudinal axis of the tool from an end part of the tool housing into a fluid flowing in the borehole;

receiving, by the longitudinal transducer, a reflected signal from reflective entrained surfaces in the fluid in the borehole along a longitudinal direction;

measuring a capacitance in a capacitance measurement between at least two electrodes of the plurality of electrodes arranged spaced apart around the longitudinal axis in the periphery of the circumferential surface of the tool housing, thereby determining properties of the fluid surrounding the tool effecting the capacitance between said at least two electrodes;

determining flow velocity of the flowing fluid from the transmitted probing signals and received reflected signals;

determining properties of the fluid surrounding the tool from the capacitance measurement indicating a type of fluid flowing;

sending a set of the determined flow velocity and the determined properties of the fluid to a computation and data storing unit;

adjusting the type of fluid flowing based on the determined flow velocity of the fluid or adjusting the flow velocity of the fluid based on the determined type of fluid flowing; and adjusting one or both of a frequency of the transducer and a transmitting angle of the transducer based on the measured capacitance.

14. A method according to claim 13, further comprising: measuring a set of calibration flow and capacitance measurements in a vertical part of the borehole above a heel of the borehole.

15. A method according to claim 13, further comprising: sending at least part of the flow and capacitance measurements to an uphole data processor for being received by a user.

16. A method according to claim 13, further comprising: selectively choosing a time interval during which a plurality of Doppler shifts are measured so that a scattering velocity profile is determined based on capacitance measurements made during the time interval.

17. A method according to claim 13, further comprising: sending data obtained by the capacitance measurements to the user uphole only if the calculated flow velocity falls outside a predefined range.

18. A downhole tool according to claim 1, wherein the probing signals of the longitudinal transducer cover angles around the entire circumference of the downhole tool.

19. A downhole tool according to claim 1, wherein the processing system is configured to adjust a frequency of the probing signal based on the capacitance between at least two electrodes.

20. A downhole system for making measurement of a fluid inside of a borehole or borehole casing, the downhole system comprising:
a downhole tool including a tool housing having a circumferential surface extending along and around a longitudinal axis of the downhole tool and having a circumference which is perpendicular to the longitudinal axis, a transducer configured to transmit a probing signal longitudinally from an end part of the tool housing and to receive a reflected signal, and a plurality of electrodes arranged spaced apart around the longitudinal axis in the periphery of the circumferential surface of the tool housing; and
a processing system coupled to the downhole tool and configured to:
receive information about the reflected signal received by the transducer;
receive capacitance measurements between two electrodes in all combinations of the plurality of electrodes indicating a type of fluid flowing; and
adjust one or more parameters of the transducer based on the capacitance measurements, wherein adjusting the one or more parameters of the transducer based on the capacitance measurements includes adjusting one or both of a frequency of the transducer and a transmitting angle of the transducer based on the capacitance measurements.

21. The downhole system of claim 20, wherein the processing system is disposed inside of the tool housing.

22. The downhole system of claim 20, wherein the processing system is further configured to: determine flow velocity of a fluid in the vicinity of the downhole tool from consecutively received reflected signals from the transducer, determine properties of the fluid using the capacitance measurements indicating the type of fluid flowing, and adjust at least one of the determined flow velocity based on the capacitance measurements and the determined type of fluid flowing based on the consecutively received reflected signals from the transducer.

23. The downhole system of claim 20, wherein the processing system is disposed inside of the tool housing and is further configured to:
determine whether the determined flow velocity of the fluid is outside of a predetermined range, and
only if the calculated flow velocity is determined to be outside of the predefined range, transmit the received capacitance measurements to an uphole data receiver.

24. The downhole system of claim 20, wherein adjusting the transmitting angle includes moving the transducer relative to the longitudinal axis.

* * * * *